(12) United States Patent
Matthews et al.

(10) Patent No.: US 6,427,351 B1
(45) Date of Patent: Aug. 6, 2002

(54) ARTHROSCOPIC MEASURING DEVICE

(75) Inventors: Leslie Matthews, Lutherville, MD (US); Eric Hubbard, Modesto; Robert-Jan Enzerink, Tracey, both of CA (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/466,312

(22) Filed: Dec. 17, 1999

Related U.S. Application Data

(60) Provisional application No. 60/113,981, filed on Dec. 28, 1998.

(51) Int. Cl.$^7$ .............................. A61B 5/103; G01B 5/14
(52) U.S. Cl. ......................... 33/512; 33/679.1; 33/542; 600/587
(58) Field of Search ........................... 33/511, 512, 700, 33/701, 679.1, 542, 544.4, 555.1, 555.2, 555.3, 806, 792, 794, 802; 600/587, 591, 588, 594, 550

(56) References Cited

U.S. PATENT DOCUMENTS

| | | | | |
|---|---|---|---|---|
| 2,454,246 A | * | 11/1948 | Worthen | 33/542 |
| 3,274,692 A | * | 9/1966 | Morrison | 33/542 |
| 4,016,867 A | * | 4/1977 | King et al. | 33/512 |
| 4,204,548 A | | 5/1980 | Kurz | |
| 4,226,025 A | * | 10/1980 | Wheeler | 33/512 |
| 4,362,167 A | | 12/1982 | Nicolai et al. | |
| 4,483,075 A | * | 11/1984 | Kundin | 33/512 |
| 4,779,349 A | * | 10/1988 | Odensten et al. | 33/512 |
| 5,010,892 A | | 4/1991 | Colvin et al. | |
| 5,379,754 A | * | 1/1995 | Tovey et al. | 33/512 |
| 6,039,701 A | * | 3/2000 | Sliwa et al. | 600/591 |

FOREIGN PATENT DOCUMENTS

| JP | 0157101 | * | 9/1982 | 33/512 |
|---|---|---|---|---|

\* cited by examiner

*Primary Examiner*—Christopher W. Fulton
(74) *Attorney, Agent, or Firm*—Barnes & Thornburg

(57) ABSTRACT

A device and a method for measuring distances between two points is described. In particular, the device and method may be used in a surgical setting. In one embodiment, the device comprises an extension for extending into the body through an incision, the extension having a distal tip for insertion into the body and a proximal handle for remaining outside the body; a first measuring end and a second measuring end at the distal tip, the first and second measuring ends at a predetermined angle from each other and defining a distance between the first and second measuring ends, the first measuring end being movable relative to the distal tip, the first and second measuring ends being rounded; and an actuator at the proximal handle for moving the first measuring end relative to the distal tip.

24 Claims, 4 Drawing Sheets

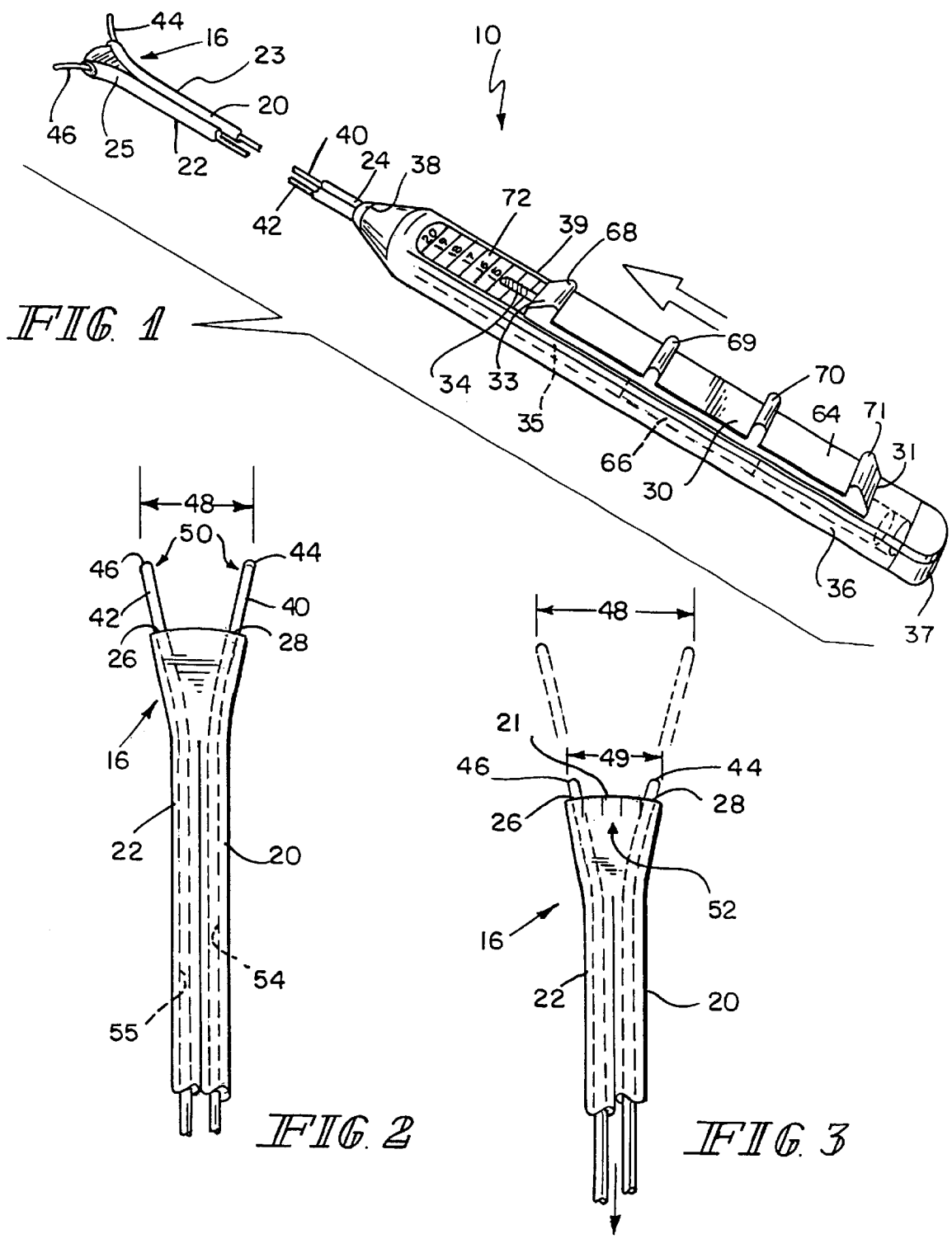

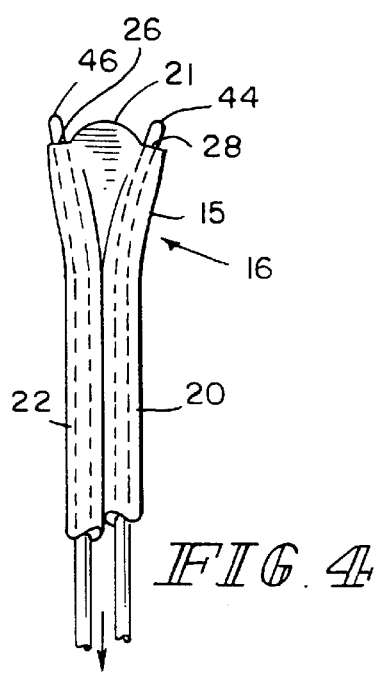
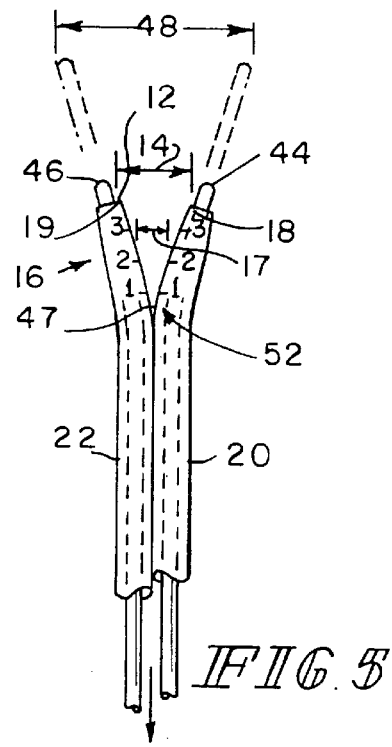
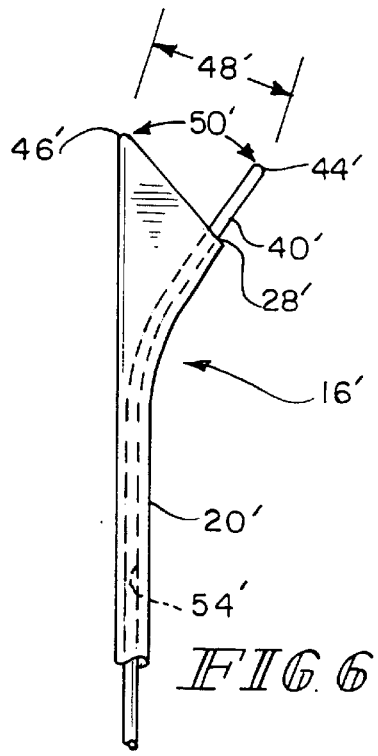
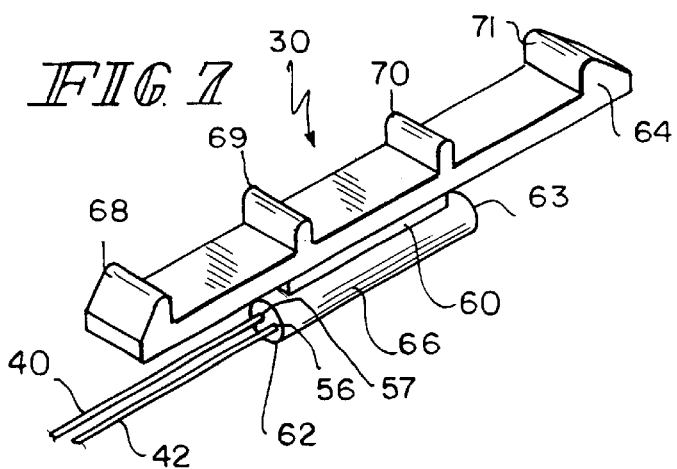

ARTHROSCOPIC MEASURING DEVICE

This application claims priority under 35 U.S.C. §119(e) to U.S. Provisional Application No. 60/113,981, filed Dec. 28, 1998, which is expressly incorporated by reference herein.

FIELD OF THE INVENTION

The present invention relates to a device for measuring distances, lengths, and widths, and more particularly to a device for measuring distances between two points in a surgical setting.

BACKGROUND AND SUMMARY OF THE INVENTION

In many surgical settings, it is often necessary for the surgeon to make measurements. Due to the confined spaces of arthroscopic surgery, measuring distances is often quite difficult, particularly when the measurement needed is larger than the size of the incision or transverse to the direction of extension of the arthroscopic instruments. Arthroscopic knee surgery provides many such situations. For example, it may be helpful if a surgeon could measure the size of a defect in the condyle of a knee, to aid in choosing the appropriate method to repair the defect.

The present invention comprises a device designed to make measurements between two points within confined spaces. such as within an arthroscopic surgical site. Preferably, the device may be used to make measurements which are not only larger than the incision but also transverse to the direction of extension of arthroscopic instruments.

The device of the present invention is an instrument comprising an extension for extending into an incision, with a tip for insertion into the incision and a handle for remaining outside the body. The tip comprises a pair of measuring ends, the measuring ends at a predetermined angle from each other, and at least one of the measuring ends being movable relative to the tip. An actuator at the handle moves at least one of the measuring ends relative to the tip.

In a preferred embodiment, a pair of elongated tubes are provided to house a pair of wires. The tubes extend from a handle to a measuring tip. An actuator, comprising a button positioned in the handle, is connected to the wires. As the device is operated, the wires extend out of the tip at a predefined angle. Calibrations are provided on the handle to correspond to the distance between the tips of the wires. Thus, when the tip is inserted into an incision, distances transverse to the direction of the shaft can be measured quickly and easily.

Preferably the extension and retraction of the measuring wires is controlled by a button located on the handle of the device. Ridges on the button allow the user to operate the device while gripping the device in a comfortable manner. In an alternative embodiment, the wires are controlled by an actuator comprising a plunger mechanism, in which the user pushes the plunger into the handle, which in turn controls extension and retraction of the wires. Other arrangements are possible within the scope of this invention.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 1 is a prospective view of a measuring device of this invention, including a handle, a pair of tubes extending distally from the handle and terminating in a tip, a button seated in the handle, and a pair of wires protruding from the tip;

FIG. 2 is a top view of the tip of the measuring device of FIG. 1;

FIG. 3 is similar to FIG. 2, except showing gradations for small measurements,

FIG. 4 is similar to FIG. 2, except showing an alternative embodiment including a rounded front surface;

FIG. 5 is similar to FIG. 2, except showing an alternative embodiment having a gap between the wires at the tip;

FIG. 6 is similar to FIG. 2, except showing an alternative embodiment including one wire;

FIG. 7 is a perspective view of the button of FIG. 1, showing wires extending distally therefrom;

DETAILED DESCRIPTION OF THE DRAWINGS

Figure 8:
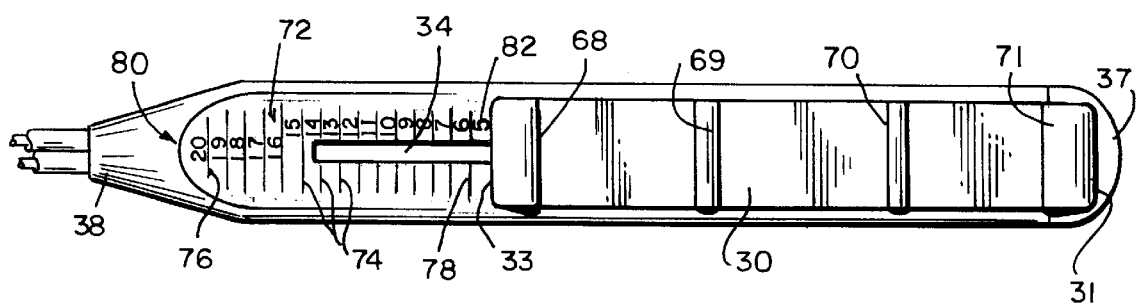
FIG. 8 is a top elevational view of the handle of FIG. 1, showing the button and calibrations.

FIG. 1 shows generally a measuring device 10 of this invention. Device 10 is provided with a handle 36, an extension 23 which extends distally from handle 36, and a button 30 which slides along a top face 39 of handle 36. Handle 36 has a proximal end 37, a distal end 38, and an axial cavity 35 which extends therebetween. A slot 34 also extends proximo-distally along handle 36 and communicates with axial cavity 35. A slide 64 portion of button 30 slides along top face 39 and a rod 66 portion of button 30 slides within axial cavity 35. Slide 64 is connected to rod 66, by means of a block 60 (seen in FIG. 7), which slides in slot 34. Extension 23 comprises a pair of tubes 20, 22. Tubes 20, 22 are provided with a distal end 25 and a proximal end 24. Tubes 20, 22 extend distally from handle 36, with proximal end 24 of tubes 20, 22 affixed to distal end 38 of handle 36. As best seen in FIG. 2, tubes 20, 22 are provided with a pair of passageways 54, 55, which terminate distally at a pair of apertures 26, 28. Proximally, passageways 54, 55 communicate with axial cavity 35. Referring to FIGS. 1 and 2, a pair of wires 40, 42 extends distally from rod 66. Wires 40, 42 extend from rod 66 through passageways 54, 55 in tubes 20, 22, to a tip 16 at distal end 25 of tubes 20, 22.

In operation, the user may push button 30 distally or pull button 30 proximally. As button 30 is pushed distally within handle 36, in the direction indicated by the arrow shown in FIG. 1, wires 40, 42 are also pushed distally and extend through apertures 26, 28 at tip 16. The more button 30 is pushed distally, the farther wires 40, 42 emerge from tip 16, and the greater a distance 48 (shown in FIG. 2) between a pair of measuring ends 44, 46. A set of calibrations 72 adjacent to button 30 on a top face 39 of button 30 corresponds to distance 48 between measuring ends 44 and 46. Thus, distances may be measured with measuring ends 44 and 46, and such distances may be read proximally on calibrations 72 of handle 36.

As illustrated in FIG. 2, wires 40 and 42 emerge from apertures 26, 28 at a predetermined angle 50, for example 20°. As the distance from tip 16 to measuring ends 44 and 46 increases, angle 50 remains the same, but transverse distance 48 between ends 44 and 46 increases. Thus, calibrations 72 may be provided for any given angle 50. Instruments with various angles 50 may be provided for use in a variety of applications, even up to 180° for measurements which are truly transverse to the incision. Similarly, the length of tubes 20, 22 may vary depending on the application.

Referring now to FIG. 3, measuring ends 44 and 46 are shown only slightly extended through apertures 26, 28. In this position, measuring ends 44 and 46 are already spaced apart by somewhat more than the width of tip 16, as indicated by distance 49. Because wires 40, 42 emerge from apertures 26, 28 in a spaced-apart arrangement, calibrations 72 (shown in FIG. 1) on handle 36 start at a measurement which is larger than zero. A set of gradations 52 on a front surface 21 of tip 16 provides for measurements which are smaller than the smallest of calibrations 72. In arthroscopic applications, such gradations 52 may be visualized through use of an arthroscopic camera. Thus, the device 10 of the present invention may provide for continuous measurement from zero to the largest of calibrated measurements 72. As illustrated in FIG. 3, front surface 21 is provided with, for example, four gradations 52, which could correspond to measurements of 1 to 4 mm and calibrations 72 start at 5 mm, which would correspond to the distance between measuring ends 44 and 46 as they begin to emerge from tip 16, as shown by distance 49 in FIG. 3. However, the measurements described above are exemplary only. The number and size of gradations 52 may vary with the application.

FIGS. 4–6 illustrate alternative embodiments for tip 16. In FIG. 4, front surface 21 is rounded, to provide for easier insertion into an operative site. Because front surface 21 is rounded, it may be more difficult to provide gradations on front surface 21. Instead, it may be preferred to provide the gradations on a more linear surface, such as side surface 15 (gradations not shown).

The embodiment of FIG. 5 is quite similar to the embodiment shown in FIGS. 3 and 4. However, unlike the embodiment shown in FIGS. 3 and 4, there is no front surface bridging tubes 20, 22. Instead, in this embodiment, tubes 22, 22 provide a valley 47. As illustrated, three gradations 52, corresponding to measurements of 1 to 3 mm, provide for small measurements. A width 14 of an absolute distal terminus 12 corresponds to a measurement of 4 mm, and calibrations can start at 5 mm, thus providing for continuous measurements. However, as with the embodiment illustrated in FIG. 3, the number and size of gradations 52 may vary with the application.

An alternative embodiment is for a tip 16' to terminate at a single fixed point 46', as shown in FIG. 6. A measuring device of this embodiment would be provided with only one tube 20' and only a single wire 40' for extending from and retracting into a tube 54' at orifice 28'. Single wire 40' would be offset from the point by a predetermined angle 50'. Measurements would be taken as a distance 48' from fixed point 46' to measuring end 44' of wire 40'. As with other embodiments, angle 50' may vary with application, and may include angles as small as 0° and as large as 180°. As with the illustrative embodiment, one skilled in the art could easily determine the proper calibrations.

FIG. 7 is a perspective view of button 30 as it appears separately from handle 36. Button 30 is provided with slide 64, rod 66, and block 60. Rod 66 is positioned and sized to slide in a proximo-distal direction within axial cavity 35 of handle 30. Slide 64 is designed to lay mostly or completely exterior to top face 39 of handle 30. Block 60 connects rod 66 to slide 64, and block 60 is designed to slide within slot 34. Wires 40, 42 extend distally from a distal face 62 of rod 66. As shown, wires 40, 42 are embedded in distal face 62 of block 66 by means of a pair of orifices 56, 57. However, other attachment configurations are possible and should be considered within the scope of this invention.

Referring to FIG. 8, slide 64 of button 30 has a proximal end 31, a distal end 33, and a plurality of ridges 68, 69, 70, 71 between proximal end 31 and distal end 33. Button 30 is shown in a proximal position, in which proximal end 31 of slide 64 is adjacent proximal end 37 of handle 36. When button 30 is in this position, wires 40, 42 are preferably completely retracted within tubes 20, 22 and do not extend beyond orifices 26, 28 at tip 16 (not shown). The user may use any one or more of ridges 68, 69, 70, 71 to slide button 30 distally. As button 30 is moved distally, distal end 33 of slide 64 will move along calibrations 72. When distal end 33 of slide 64 reaches one of a plurality of calibration lines 74, a corresponding calibration marking 80 indicates distance 48 between measuring ends 44 and 46 (shown in FIG. 2). For example, when distal end 33 of slide 64 contacts a first calibration line 78, distance 48 between measuring ends 44 and 46 would be the distance indicated by first calibration marking 82. In the illustrative example, this would be 5 mm, and the position of wires 40, 42 at tip 16 may appear as shown in FIG. 3. The position shown in FIG. 1 illustrates button 30 in a more intermediate position.

Figure 9:
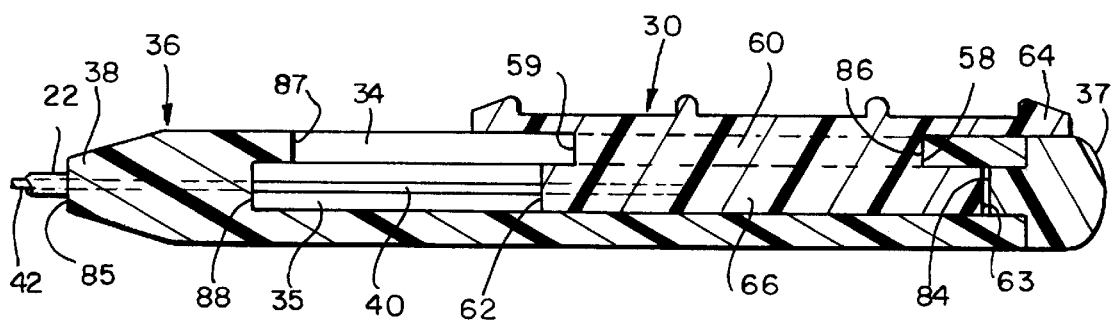
FIG. 9 is a side cross-sectional view of the handle of FIG. 1, showing the button in a proximal location.
Figure 10:
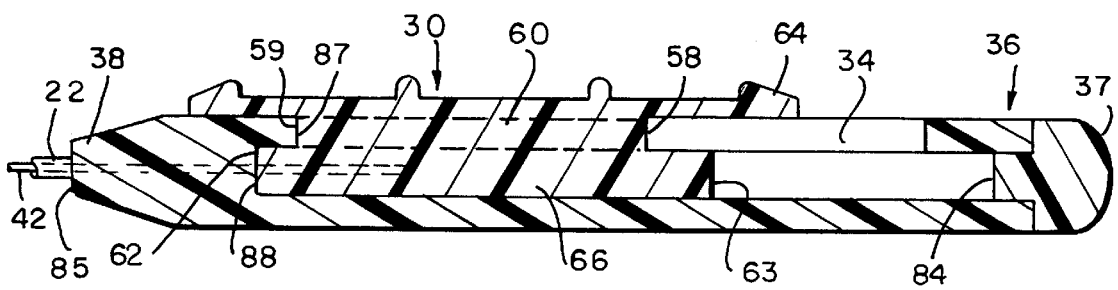
FIG. 10 is similar to FIG. 9, except showing the button in a distal location.

As seen in FIG. 1 the illustrative embodiment of measuring device 10 is provided with slot 34 in handle 36 which, as illustrated, can be seen adjacent to proximal edge 31 and adjacent to distal edge 33 of button 30. Also, handle 36 is provided with axial cavity 35. As shown, axial cavity 35 extends through most of handle 36. FIGS. 9 and 10 illustrate device 10 configured such that axial cavity 35 and slot 34 prevents excessive proximo-distal movement of button 30, restricting button 30 and wires 40, 42 to a preset length of travel. FIG. 9 illustrates handle 36 with button 30 in the proximal-most position. In this position, a proximal end 58 of block 60 is in contact with a proximal end 86 of slot 34. Also, a proximal face 63 of rod 66 is in contact with proximal end 84 of axial cavity 35. Thus, no further proximal movement of button 30 is possible. FIG. 10 illustrates button 30 in the distal-most position. A distal end 59 of block 60 is in contact with a distal end 87 of slot 34. In the illustrated embodiment, axial cavity 35 extends all the way to distal end 38 of handle 36, in order to provide passage for wires 40, 42 to extend to tubes 20, 22. Thus distal face 62 of rod 66 does not contact the absolute distal end 85 of axial cavity 35. However, axial cavity 35 narrows at a transition 88, which provides additional restraint. Alternatively, since proximal end 86 and distal end 87 of slot 34 provide stops for button 30, axial cavity 35 may maintain the same diameter throughout the length of handle 36. Additional stability is provided by block 60 and slot 34, which prevent button 30 from twisting relative to handle 36 and prevents wires 40, 42 from twisting within handle 36. However, other methods of constraining unwanted motion are within the scope of this invention. It will be understood that constraint against excessive proximo-distal and twisting motion is a preferred embodiment. Other configurations are possible within the scope of the present invention.

The illustrative embodiment has been described with the button 30 directly connected to wires 40, 42 inside handle 36. However, button 30 may be connected to wires 40, 42 by a series of gears or pulleys, or by various other mechanisms. Also, the illustrative embodiments comprise mechanical calibrations and indicators. Various other mechanisms for indicating the measurements are within the scope of this invention. For instance, an electronic display indicator with digital calibrations may be used. These and other alternative embodiments are within the scope and spirit of this invention.

Figure 11:
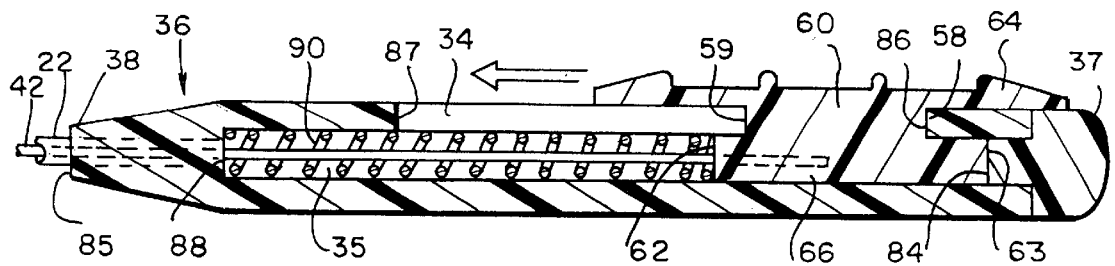
FIG. 11 is similar to FIG. 9, except further comprising a spring to bias the button to the proximal position.

In one embodiment of this invention, rod 66 and axial cavity 35 may be in sufficient frictional contact that button 30 will remain fixed in position relative to handle 36 until the user pushes or pulls button 30. The button 30 will then remain fixed in its new position until the user once again changes the position. In an alternative embodiment of this invention, as shown in FIG. 11, a spring 90 may be provided within handle 36. As shown in FIG. 11, spring 90 is located within axial cavity 35 between rod 66 and transition 88 of axial cavity 35. Spring 90 bears on transition 88 and distal face 62 of rod 66, and spring 90 biases rod 66 against proximal end 84 of axial cavity 35. In this position, wires 40, 42 would be, preferably, fully retracted within tubes 20, 22. Distal pressure on button 30 would push button 30 distally, which would push wires 40, 42 out from apertures 26, 28. However, once the pressure is released, spring 90 would cause wires 40, 42 to retract automatically to the starting position, as shown in FIG. 11.

The measuring device of FIG. 1 may be used by inserting tip 16 and a portion of extension 23 into a small incision of a patient. Button 30 is then used to push wires 40, 42 through apertures 26, 28 until measuring ends 44, 46 span the distance to be measured. Handle 36 remains outside of the patient's body, and the distance between measuring ends 44, 46 may be read on handle 36 as the calibration 72 then indicated.

Figures 12, 13:
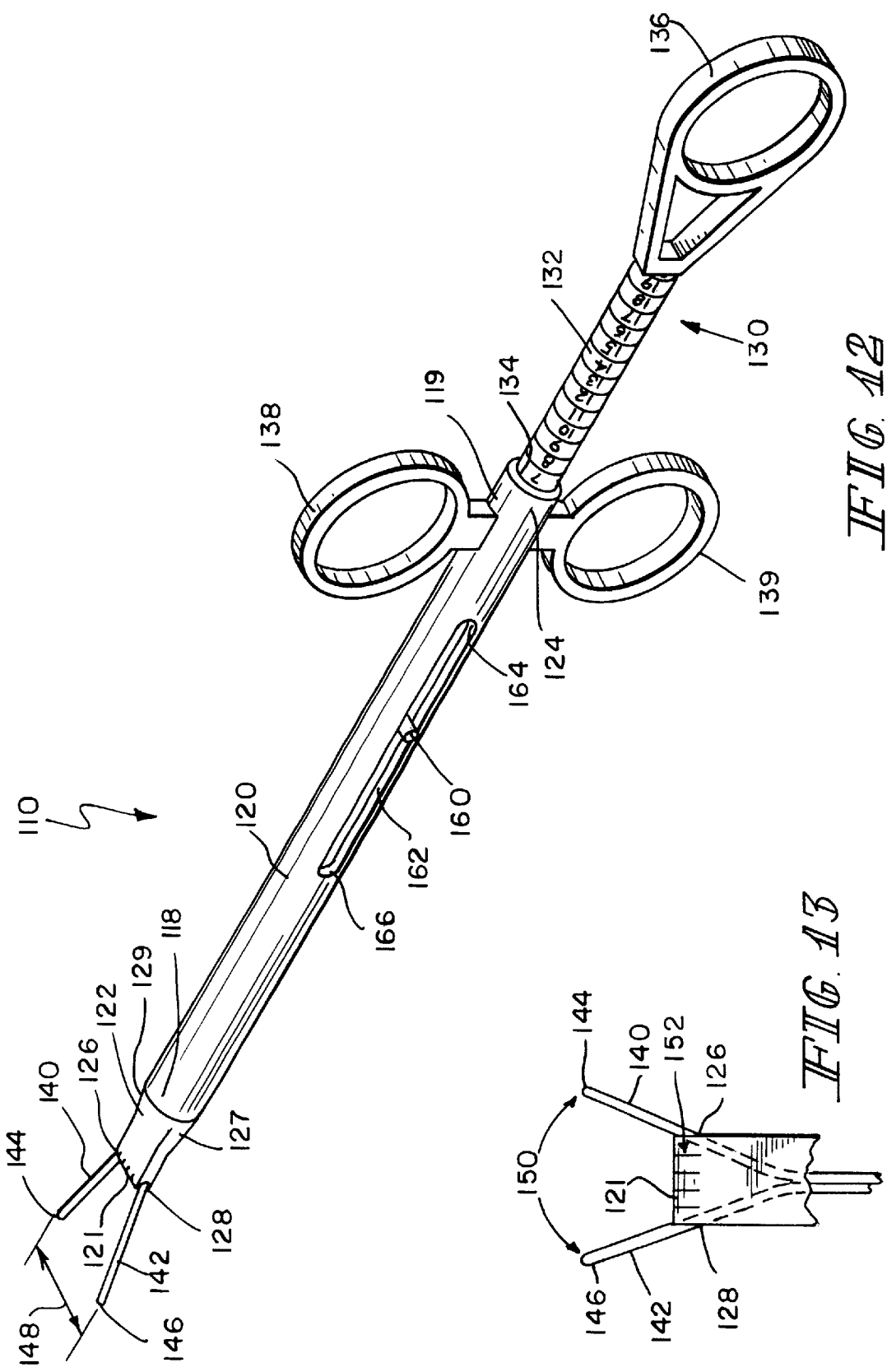
FIG. 12 is a prospective view of an alternative embodiment of a measuring device of this invention.
FIG. 13 is a top view of the tip of the measuring device of FIG. 12.

FIGS. 12 and 13 illustrate an alternative embodiment 110 of the present invention. FIG. 12 shows generally measuring device 110. Device 110 is provided with a sleeve 120 and a plunger 130. Preferably, sleeve 120 is elongated. Sleeve 120 is provided with a tip 122 at a distal end 118 and a head 124 at a proximal end 119. Plunger 130 telescopes within sleeve 120 at head 124. As plunger 130 is pushed within sleeve 120, a pair of wires 140, 142 are pushed out of a pair of apertures 126, 128 at tip 122. The further plunger 130 is pushed within sleeve 120, the more of wires 140, 142 extend from tip 122, and the greater a distance 148 between a pair of measuring ends 144 and 146. A set of calibrations 132 on plunger 130 corresponds to distance 148 between measuring ends 144 and 146.

As illustrated in FIG. 13, wires 140, 142 are separated by a predetermined angle 150, for instance 2020. As the distance from a front surface 121 to the measuring ends 144, 146 increases, angle 150 remains the same, but the distance 148 (shown FIG. 12) between measuring ends 144, 146 increases. Thus, as with device 10, one skilled in the art could easily calculate the appropriate calibrations 132 for a given angle of 150. Instruments with various angles 150 could be provided for use in a variety of applications.

As best seen in FIGS. 12 and 13, wires 140, 142 emerge through apertures 126, 128. As illustrated, apertures 126, 128 are located in side surfaces 127, 129 adjacent to the front surface 121 of tip 122. Thus, when wires 140, 142 emerge through apertures 126, 128, they are already spaced apart by the width of tip 122. As seen in FIG. 13, a set of gradations 152 at front surface 121 provide for measurements which are smaller than the first of calibrations 132. As illustrated. front surface 121 is provided with four gradations 152, which could correspond to measurements of 0 to 4 mm, the width of tip 122 may correspond to 5 mm, and calibrations 132 may start at 6 mm. However, as with angle 150, the number and size of gradations may vary with the application.

Referring again to FIG. 12, distance 148 between measuring ends 144, 146 may be read as the specific calibration marking 132 which is adjacent to an opening 134 in a sleeve head 124. In an alternative embodiment, a window may be provided within sleeve 120, in which the calibration would appear which corresponds to distance 148.

As illustrated, measuring device 110 is provided with a pair of finger rings 138, 139 on sleeve 120 and a thumb ring 136 on plunger 130. This configuration allows the user both to push and pull the plunger 130 with relative ease. However, numerous other gripping configurations are possible.

The illustrative embodiment is provided with a slot 162 in sleeve 120. A pin 160, affixed to a portion of plunger 130 inside of sleeve 120, engages slot 162. Proximal end 164 and distal end 166 of slot 162 restrain pin 160 and prevent excessive movement of pushing or pulling on plunger 130. Also, pin 160 and slot 162 prevent plunger 130 and wires 140, 142 from twisting within sleeve 120. Other configurations are possible within the scope of the present invention.

It will be understood that the arthroscopic measuring device of this invention may be substantially straight and rigid, for measuring distances which are transverse to the straight longitudinal axis of the device. It will also be understood that the tubes and wires may be curved, for arthroscopic applications where a straight instrument would not be useful. Finally, the tubes and wires may be made of somewhat flexible materials, which may bend as needed in arthroscopic surgery.

Although the invention has been described in detail with reference to preferred embodiments, variations and modifications exist within the scope and spirit of the invention as described and defined in the following claims.

What is claimed is:

1. An arthroscopic instrument for measuring the distance between two points internal to a body of a patient comprising:

an extension for extending into the body through an incision, the extension having a distal tip for insertion into the body and a proximal handle for remaining outside the body;

a first measuring end and a second measuring end at the distal tip, the first and second measuring ends at a predetermined angle from each other and defining a distance between the first and second measuring ends, the first and second measuring ends being movable relative to the distal tip, the first and second measuring ends being rounded; and an actuator at the proximal handle for moving the first measuring end relative to the distal tip.

2. The arthroscopic instrument of claim 1 wherein the first measuring end consists of a distal end of a first wire, the first wire further comprising a proximal end connecting to the actuator, and the second measuring end consists of a distal end of a second wire, the second wire further comprising a proximal end connecting to the actuator.

3. The arthroscopic instrument of claim 1 wherein the actuator comprises a button which is movable relative to the handle.

4. The arthroscopic instrument of claim 1 wherein the handle is provided with an axial cavity and the actuator comprises a plunger at least partially disposed within the axial cavity for movement therein.

5. The arthroscopic instrument of claim 1 further comprising a set of calibrations and an indicator, whereby movement of the actuator causes movement of the first and second measuring ends relative to the distal tip and corresponding movement of the indicator relative to the calibrations.

6. The arthroscopic instrument of claim 5 wherein the indicator is located on the handle.

7. A measuring device for use in surgical settings comprising:
- a handle;
- a measuring tip having a pair of apertures;
- an elongated extension having at least one passageway, the extension extending distally from the handle to the measuring tip;
- a button in slidable engagement with the handle; and
- a pair of wires coupled to the button, the wires extending through the passageway of the extension to the apertures of the measuring tip, each of the pair of wires being rounded;
  - whereby when the button is moved, the wires extend through the tip at a predefined angle.

8. The measuring device of claim 7 wherein the pair of wires comprise a pair of measuring ends defining a distance therebetween, the handle further comprises a set of calibrations, and the device further comprises an indicator, whereby after the button is moved the indicator identifies the calibration corresponding to the distance between the measuring ends.

9. The measuring device of claim 8 wherein the indicator comprises a distal edge of the button.

10. The measuring device of claim 8, further comprising a set of gradations at the measuring tip for measuring distances smaller than indicated by the calibrations.

11. The measuring device of claim 7 wherein the predefined angle is fixed at approximately 20°.

12. The measuring device of claim 7 wherein the predefined angle is fixed at an angle greater than 20°.

13. The measuring device of claim 7 wherein the extension comprises a pair of hollow tubes, each housing one of the pair of wires.

14. The measuring device of claim 7, further comprising an axial cavity within the handle and a spring disposed within the axial cavity, the spring contacting a distal surface of the button and biasing the button proximally.

15. The measuring device of claim 7 further comprising a pair of tubes extending from the handle to the measuring tip, wherein each wire extends through its respective tube.

16. A measuring device comprising:
- a handle;
- a tip;
- an extension connecting the handle to the tip;
- a first measuring end and a second measuring end extending at a fixed angle from the tip, the first and second measuring ends movable distally relative to the tip, the first and second measuring ends being rounded; and
- an actuator movably coupled to the handle and connected to the first and second measuring ends;
  - whereby movement of the actuator causes corresponding distal movement of the first and second measuring ends and alters a distance between the first and second measuring ends.

17. The device of claim 16 wherein the handle further comprises a set of calibrations and the actuator further comprises an indicator, whereby movement of the actuator causes the indicator to select the calibration corresponding to the distance between the first and second measuring ends.

18. The device of claim 16 wherein the actuator further comprises a set of calibrations and the handle comprises an indicator, whereby movement of the actuator causes the indicator to select the calibration corresponding to the distance between the first and second measuring ends.

19. The device of claim 16 wherein the first measuring end comprises a distal end of a first wire, the first wire having a proximal end fixed to the actuator, and the second measuring end comprises a distal end of a second wire, the second wire having a proximal end fixed to the actuator.

20. A method for measuring a space in an arthroscopic setting comprising the steps of:
- providing an arthroscopic measuring device comprising a first and a second measuring end at a distal tip, the first and second measuring ends at a predetermined angle from each other and defining a distance between the first and second measuring ends, the first and second measuring ends being rounded, the first measuring end movable relative to the distal tip; a set of calibrations; and an actuator at a proximal handle for correspondingly moving the first measuring end relative to the distal tip and moving the indicator relative to the calibrations;
- inserting the distal tip into an incision;
- moving the actuator until the distance between the measuring ends about equals the distance to be measured; and
- determining the calibration which corresponds to the distance between the measuring ends.

21. An arthroscopic instrument for measuring the distance between two points internal to a body of a patient comprising:
- an extension for extending into the body through an incision, the extension having a distal tip for insertion into the body and a proximal handle for remaining outside the body;
- a first measuring end and a second measuring end at the distal tip, the first and second measuring ends at a fixed predetermined acute angle from each other and defining a distance between the first and second measuring ends, the first measuring end being movable relative to the distal tip; and
- an actuator at the proximal handle for moving the first measuring end relative to the distal tip.

22. An arthroscopic instrument for measuring the distance between two points internal to a body of a patient comprising:
- an extension for extending into the body through an incision, the extension having a distal tip for insertion into the body and a proximal handle for remaining outside the body, the distal tip terminating in a single fixed point and having an orifice spaced apart from the single fixed point;
- a first measuring end comprising a rounded terminus of a wire extending through the orifice and being movable relative to the distal tip, a second measuring end comprising the single fixed point of the distal tip and being fixed relative to the distal tip, and wherein the first and second measuring ends are at a predetermined angle from each other and defining a distance between the first and second measuring ends;
- an actuator at the proximal handle connected to the wire, for moving the first measuring end relative to the distal tip.

23. An arthroscopic instrument for measuring the distance between two points internal to a body of a patient comprising:

an extension for extending into the body through an incision, the extension having a distal tip for insertion into the body and a proximal handle for remaining outside the body;

a first measuring end consisting of a distal end of a first wire and a second measuring end at the distal tip consisting of a distal end of a second wire, the first and second measuring ends at a predetermined angle from each other and defining a distance between the first and second measuring ends, the first and second measuring ends being movable relative to the distal tip; and an actuator at the proximal handle for moving the first and second measuring ends relative to the distal tip.

24. A method for measuring a space in an arthroscopic setting comprising the steps of:

providing an arthroscopic measuring device comprising a first and a second measuring end at a distal tip, the first and second measuring ends at a predetermined angle from each other and defining a distance between the first and second measuring ends, the first and second measuring ends being rounded, the first measuring end movable relative to the distal tip; a set of calibrations; and an actuator at a proximal handle for correspondingly moving the first measuring end relative to the distal tip and moving the indicator relative to the calibrations, the arthroscopic measuring device further comprising a set of gradations at the distal tip for measuring distances smaller than indicated by the calibrations;

inserting the distal tip into an incision;

moving the actuator until the distance between the measuring ends about equals the distance to be measured; and determining the calibration or gradation that corresponds to the distance between the measuring ends.

* * * * *